United States Patent [19]
Lai

[11] Patent Number: 5,922,761
[45] Date of Patent: Jul. 13, 1999

[54] METHODS FOR IN VIVO REDUCTION OF IRON LEVELS AND COMPOSITIONS USEFUL THEREFOR

[75] Inventor: Ching-San Lai, Encinitas, Calif.

[73] Assignee: Medinox, Inc., San Diego, Calif.

[21] Appl. No.: 08/708,552

[22] Filed: Sep. 6, 1996

[51] Int. Cl.$^6$ .......................... A61K 31/27; A61K 31/40
[52] U.S. Cl. ...................... 514/476; 514/479; 514/480; 514/481; 514/484; 514/423
[58] Field of Search ................................. 514/423, 476, 514/479, 480, 481, 484

[56] References Cited

U.S. PATENT DOCUMENTS

| | | | |
|---|---|---|---|
| 4,056,621 | 11/1977 | Brown et al. | 424/273 |
| 4,160,452 | 7/1979 | Theeuwes | 128/260 |
| 4,173,644 | 11/1979 | Brown et al. | 424/270 |
| 4,256,108 | 3/1981 | Theeuwes | 128/260 |
| 4,265,874 | 5/1981 | Bonsen et al. | 424/15 |
| 4,894,393 | 1/1990 | Nguyen et al. | 514/476 |
| 5,380,747 | 1/1995 | Medford et al. | 514/423 |
| 5,430,058 | 7/1995 | Shanzer et al. | 514/575 |

OTHER PUBLICATIONS

Al–Refaie et al., "Efficacy and Possible Adverse Effects of the Oral Iron Chelator 1,2–Dimethyl–3–Hydroxypyrid–4–One (L$_1$) in Thalassemia Major" *Blood* 80(3):593–599 (1992).

Biemond et al., "Intraarticular Ferritin–Bound Iron in Rheumatoid Arthritis" *Arthritis Rheum.* 29(10):1187–1193 (1986).

Biemond et al., "Iron Mobilization from Ferritin by Superoxide Derived from Stimulated Polymorphonuclear Leukocytes" *J. Clin. Invest.* 73:1576–1579 (1984).

De Sousa et al., "Iron, Iron–binding Proteins and Immune System Cells*"* *Ann. N.Y. Acad. Sci.* 526:310–323 (1988).

De Virgiliis et al., "Depletion of trace elements and acute ocular toxicity induced by desferrioxamine in patients with thalassaemia" *Arch. Dis. Chil.* 63:250–255 (1988).

Dizdaroglu and Bergtold, "Charaterization of Free Radical-–Induced Base Damage in DNA at Biologically Relevent Levels" *Anal. Biochem.* 156:182–188 (1986).

Guyader et al., "Evaluation of Computed Tomography in the Assessment of Liver Iron Overload" *Gastroenterol.* 97:737–743 (1989).

Haber and Weiss, "The Catalytic Decomposition of Hydrogen Peroxide by Iron Salts" *Proc. R. Soc. Ser. A.* 147:332–351 (1934).

Halliwell and Gutteridge, in Halliwell and Gutteridge, Free Radicals in Biology and Medicine, 2nd edition. Oxford: Clarendon Press, 15–19 (1989).

Harrison and Hoare, in *Metals in Biochemistry*, Chapman and Hall, New York, (1980).

Kim et al., "Loss and Degradation of Enzyme–bound Heme Induced by Cellular Nitric Oxide Synthesis" *J. Biol. Chem.* 270(11):5710–5713 (1995).

Kolaric et al., "A Phase II Trial of Cardioprotection with Cardioxane (ICRF–187) in Patients with Advanced Breast Cancer Receiving 5–Fluorouracel, Doxorubicin and Cyclophosphamide" *Oncology* 52:251–255 (1995).

Komarov and Lai, "Detection of nitric oxide production in mice by spin–trapping electron paramagnetic resonance spectroscopy" *Biochim. Biophys. Acta* 1271:29–36 (1995).

Kontoghiorghes, G. J., "Advances in oral iron chelation in man" *Int. J. Hematol.* 55:27–38 (1992).

Kontoghiorghes, G. J., "Comparative efficacy and toxicity of desferrioxamine, deferiprone and other iron and aluminium chelating drugs" *Toxicol. Letters* 80:1–18 (1995).

Lai and Komarov, "Spin trapping of nitric oxide produced in vivo in septic–shock mice" *FEBS Letters* 345:120–124 (1994).

Lai and Piette, "Hydroxyl Radical Production Involved in Lipid Peroxidation of Rat Liver Microsomes" *Biochem. Biophys. Res. Commun.* 78(1):51–59 (1977).

Muirden and Senator, "Iron in the Synovial Membrane in Rheumatoid Arthritis and Other Joint Diseases" *Ann. Rheum. Dis.* 27:38–48 (1968).

Myers et al., "Adriamycin: The Role of Lipid Peroxidation in Cardiac Toxicity and Tumor Response" *Science* 197:165–167 (1977).

Pippard et al., "Ferrioxamine Excretion in Iron–Loaded Man" *Blood* 60(2):288–294 (1982).

Proper et al., "Reassessment of the Use of Desferrioxamine B in Iron Overload" *N. Engl. J. Med.* 294(26):1421–1423 (1976).

(List continued on next page.)

*Primary Examiner*—Theodore J. Criares
*Attorney, Agent, or Firm*—Gray Cary Ware & Freidenrich LLP; Stephen E. Reiter

[57] ABSTRACT

In accordance with the present invention, there are provided methods for the in vivo reduction of free iron ion levels in a mammalian subject. The present invention employs a scavenging approach whereby free iron ions are bound in vivo to a suitable physiologically compatible scavenger. The resulting complex renders the free iron ions harmless, and is eventually excreted in the urine of the host. Further in accordance with the present invention, there are provided compositions and formulations useful for carrying out the above-described methods. An exemplary scavenger contemplated for use in the practice of the present invention is a dithiocarbamate-containing composition. This material binds to free iron ions, forming a stable, water-soluble dithiocarbamate-iron complex. The present invention relates to methods for reducing in vivo levels of free iron ions as a means of treating subjects afflicted with iron overload and non-iron overload diseases and/or conditions, such as thalassemia, anemia hereditary hemochromatosis, hemodialysis, stroke and rheumatoid arthritis. Dithiocarbamate-containing scavengers are administered to a host in need of such treatment; these scavengers interact with in vivo forming a stable dithiocarbamate-metal complex, which is then filtered through the kidneys, concentrated in the urine, and eventually excreted by the subject, thereby reducing in vivo levels of free iron ions.

40 Claims, 3 Drawing Sheets

OTHER PUBLICATIONS

Rowley et al., "Lipid peroxidation in rheumatoid arthritis: thiobarbituric acid–reactive material and catalytic iron salts in snyovial fluid from rheumatoid patients" *Clin. Sci.* 66:691–695 (1984).

Shinobu et al., "Sodium N–Methyl–D–glucamine Dithiocarbamate and Cadmium Intoxication" *Acta Pharmacol et Toxicol.* 54:189–194 (1984).

Singal et al., "Subcellular Effects of Adriamycin in the Heart: A Concise Review" *J. Mol. Cell. Cardiol.* 19:817–828 (1987).

St. Louis et al., "Comparison of oral iron chelator L1 and desferrioxamine in iron–loaded patients" *Lancet* 336:1275–1279 (1990).

Thomas et al., "The Hydrolysis Product of ICRF–187 Promotes Iron–Catalysed Hydroxyl Radical Production via the Fenton Reaction" *Biochem. Pharmacol.* 45(10):1967–72 (1993).

Voest et al., "Iron–Chelating Agents in Non–Iron Overload Conditions" *Ann. Intern. Med.* 120(6):490–499 (1994).

Vreugdenhil et al., "Efficacy and Safety of Oral Iron Chelator $L_1$ in Anaemic Rheumatoid Arthritis Patients" *Lancet* 8:1398–1399 (1989).

METHODS FOR IN VIVO REDUCTION OF IRON LEVELS AND COMPOSITIONS USEFUL THEREFOR

FIELD OF THE INVENTION

The present invention relates to methods for reducing iron levels in mammals. In a particular aspect, the present invention relates to methods for reducing free iron ion levels in mammals by administration of dithiocarbamates as scavengers of free iron ions in hosts undergoing anthracycline chemotherapy, as well as hosts suffering from iron overload or non-iron overload diseases and/or conditions, such as thalassemia, anemia, hereditary hemochromatosis, hemodialysis, stroke and rheumatoid arthritis. In a further aspect, the present invention relates to compositions and formulations useful in the methods disclosed herein.

BACKGROUND OF THE INVENTION

Iron is crucial for maintaining normal structure and function of virtually all mammalian cells (see, for example, Voest et al., in *Ann. Intern. Med.* 120:490–499 (1994) and Kontoghiorghes, G. J., in *Toxicol. Letters* 80:1–18 (1995)) Adult humans contain 3–5 g of iron, mainly in the form of hemoglobin (58%), ferritin/hemosiderin (30%), myoglobin (9%) and other heme or nonheme enzyme proteins (Harrison and Hoare, in *Metals in Biochemistry*, Chapman and Hall, New York, 1980).

Total iron levels in the body are regulated mainly through absorption from the intestine and the erythropoietic activity of the bone marrow. Upon absorption, iron is transported to various tissues and organs by the serum protein transferrin. Once transported to the target tissue or organ, iron is transported and stored intracellularly in the form of ferritin/hemosiderin. Under normal conditions, transferrin is about 30% saturated with iron in healthy individuals, and an equilibrium is maintained between the sites of iron absorption, storage and utilization. The presence of these homeostatic controls ensures the maintenance of physiological levels of not only iron, but also other essential metal ions such as copper, zinc and cobalt.

Breakdown of these controls could result in metal imbalance and metal overload, causing iron overloading toxicity and possibly death in many groups of patients, especially those with idiopathic hemochromatosis (see, for example, Guyader et al., in *Gastroenterol.* 97:737–743 (1989)). Among its toxic effects, iron is known to mediate a repertoire of oxygen related free radical reactions (see, for example, Halliwell and Gutteridge, in Halliwell and Gutteridge, Free Radicals in Biology and Medicine, 2nd edition. Oxford: Clarendon Press, 15–19 (1989)). For example, iron, particularly in the form of free iron ions, can promote the generation of reactive oxygen species through the iron-catalyzed Haber-Weiss reaction (see, for example, Haber and Weiss, in *Proc. R. Soc. Ser. A.* 147:332 (1934)) as follows:

The net result of these reactions is as follows:

The Haber-Weiss reaction is seen to produce the hydroxyl radical (.OH), a highly potent oxidant which is capable of causing oxidative damage to lipids, proteins and nucleic acids (see, for example, Lai and Piette, in *Biochem. Biophys. Res. Commun.* 78:51–59 (1977); and Dizdaroglu and Bergtold, in *Anal. Biochem.*, 156:182 (1986)).

The occurrence of iron imbalance resulting in excessive in vivo iron levels can be categorized into two conditions, namely iron-overload and non-iron overload conditions (see, for example, Voest et al., supra; Kontoghiorghes, supra). Iron-overload conditions are common in such patients as those suffering from thalassemia, sickle cell anemia, repeated blood transfusion and hereditary hemochromatosis. In such patients, transferrin is fully saturated with iron, and excess low-molecular-weight iron appears in the serum. This low-molecular-weight iron appears to originate from the iron released mainly from the liver and spleen, and from the breakdown of effete red cells. Other iron overload diseases and conditions include hereditary spherocytosis, hemodialysis, dietary or latrogenic iron intake, intramuscular iron dextran and hemolytic disease of the newborn (see, for example, Voest et al., supra; Kontoghiorghes, supra).

Non-iron overload conditions relate to situations where elevated iron levels are the result of therapeutic intervention, such as, for example, anthracycline anti-cancer therapy or inflammatory diseases such as rheumatoid arthritis. While anthracyclines such as adriamycin (doxorubicin) are effective in the treatment of a number of neoplastic diseases, these compounds have limited clinical utility due to the high incidence of cardiomyopathy (see, for example, Singal et al., in *J. Mol. Cell. Cardiol.* 30 19:817–828 (1987)).

The molecular mechanism of cardiomyopathy is now attributed to the adriamycin-induced release of iron from intracellular iron-containing proteins, resulting in the formation of an adriamycin-iron complex, which generates reactive oxygen species causing the scission and condensation of DNA, peroxidation of phospholipid membranes, depletion of cellular reducing equivalents, interference with mitochondrial respiration, and disruption of cell calcium homeostasis (see, for example, Myers et al., *Science* 197:165–167 (1977); and Gianni et al., in *Rev. Biochem. Toxicol.* 50:1–82 (1983)). On the other hand, several clinical studies have shown that patients with rheumatoid arthritis exhibit elevated low-molecular weight iron species and ferritin-bound iron levels in synovial fluid. Iron, presumably via its mediation of oxygen free radical pathways, exerts its proinflammatory effects in rheumatoid arthritis (see, for example, Muirden and Senator, in *Ann. Rheum. Dis.* 27:38–48 (1968); and Biemond et al., in *Arthritis Rheum.* 29:1187–1193 (1986)).

Iron also plays an important role in many aspects of immune and nonimmune host response (see, for example, De Sousa et al., in *Ann. N.Y. Acad. Sci.* 526:310–323 (1988)). It is known that increased concentrations of iron are deleterious to the immune system through the initiation or maintenance of inflammatory reactions (see, for example, Biemond et al., in *J. Clin. Invest.* 73:1576–9 (1984); and Rowley et al., in *Clin. Sci.* 66:691–5 (1984)). Other non-iron overload diseases and conditions include reperfusion injury, solid tumors (e.g., neuroblastoma), hematologic cancers (e.g., acute myeloid leukemia), malaria, renal failure, Alzheimer's disease, Parkinson's disease, inflammation, heart disease, AIDS, liver disease (e.g., chronic hepatitis C), microbial/parasitic infections, myelofibrosis, drug-induced lung injury (e.g., paraguat), graft-versus-host disease and transplant rejection and preservation.

Hence, not surprisingly, there has been a tremendous interest in the therapeutic use of chelators in the treatment of both iron-overload and non-iron overload diseases and conditions. A chelator (Greek, chele-claw of a crab) is a molecule forming a cyclic ring with a metal as the closing member. Hundreds of chelating agents have been designed and developed for animal and human studies. Among them, at least fifteen different chelators have been used in humans, including desferrioxamine (DF), ethylenediaminetetraacetic acid (EDTA), diethylenetriamine pentaacetic acid (DTPA) pyridoxalisonicotinoylhydrazone (PIH), 1,2-dimethyl-3-hydroxypyrid-4-one (L1) and [+] 1,2-bis-(3,5-dioxopiperazine-1-yl) propane (ICRF-187).

For the past 30 years, DF (i.e., desferrioxamine) has been the most commonly used chelating drug for the treatment of transfusional iron overload (see, for example, Pippard et al., in Blood 60:288–294 (1982); Proper et al., in N. Engl J. Med. 294:1421–1423 (1976); and St. Louis et al., in Lancet 336:1275–1279 (1990)). Patients suffering from thalassemia lived longer with the DF treatment. However, major drawbacks in the use of DF include the cost thereof (~$7,000/patient/year), which can be affordable only by a very small percentage of thalassemia patients worldwide. Another drawback to the use of DF includes the toxicity thereof, including ophthalmic and auditory toxicities as well as induction of pulmonary and renal damage.

Unlike DF, L1 (i.e., 1,2-dimethyl-3-hydroxypyrid-4-one) and related compounds are orally available iron chelators, showing promise in improving the quality of life in patients with thalassemia (see, for example, Olivieri et al., in Drugs Today 28(Suppl. A): 123–132 (1992)) and rheumatoid arthritis (see, for example, Vreugdenhil et al., in Lancet 2:1398–9 (1989)). However, the major side effects of L1 therapy include myelosuppression, fatigue, and maternal, embryo and teratogenic toxicity, which severely limits the potential clinical applications thereof (see, for example, Kontoghiorghes, in Int. J. Hematol. 55:27–38 (1992)).

Recently, ICRF-187 has been demonstrated to be effective in removing iron from the anthracycline-iron complex, therefore preventing the cardiac toxicity in cancer patients receiving adriamycin chemotherapy (see, for example, Kolaric et al., in Oncology 52:251–5 (1995)). However, when chelated with iron, the iron-ICRF-187 complex per se is also very effective in the promotion of hydroxyl radical generation via the Fenton reaction, causing oxidative damage to tissues (see, for example, Thomas et al., in Biochem. Pharmacol. 45:1967–72 (1993)). In addition, since ICRF-187 is a strong chelator (having a structure similar to EDTA), it chelates not only low-molecular-weight iron, but also chelates iron from transferrin and ferritin, as well as copper from ceruloplasmin, thus potentially affecting normal cellular iron metabolism.

Therefore, there is still a need in the art for a new class of iron chelators that are capable of removing free iron ions from body fluids, without affecting the normal cellular iron metabolism.

BRIEF DESCRIPTION OF THE INVENTION

In accordance with the present invention, methods have been developed for the in vivo reduction of free iron ion levels in a subject. The present invention employs a scavenging approach whereby free iron ions are bound in vivo to a suitable physiologically compatible scavenger, i.e., a compound capable of binding free iron ions. The resulting complex renders the free iron ions harmless, and is eventually excreted in the urine of the host. Further in accordance with the present invention, there have been developed compositions and formulations useful for carrying out the above-described methods.

An exemplary physiologically compatible scavenger contemplated for use in the practice of the present invention is a dithiocarbamate-based formulation. Dithiocarbamates according to the invention bind to free iron ions, forming a stable, water-soluble dithiocarbamate-iron complex. Dithiocarbamates are a class of low molecular-weight sulphur-containing compounds that are effective chelators (see, for example, Shinobu et al., in Acta Pharmacol et Toxicol. 54:189–194 (1984)). For example, diethyldithiocarbamate (DETC) is used clinically for the treatment of nickel poisoning.

Dithiocarbamates, such as N-methyl-D-glucamine dithiocarbamate (MGD), chelate with ferrous or ferric iron to form a stable and water-soluble two-to-one $[(MGD)_2\text{-}Fe^{2+}]$ or $[(MGD)_2\text{-}Fe^{3+}]$ complex (see, for example, Lai and Komarov, in FEBS Letters 345:120–124 (1994)). However, MGD administrated into normal rats did not chelate endogenous iron to form the $[(MGD)_2\text{-}Fe]$ complex, suggesting that MGD does not remove iron from either hemoglobin or other iron containing enzymes or proteins. On the other hand, administration of MGD into endotoxin-treated rats resulted in the formation of the $[(MGD)_2\text{-}Fe]$ complex which could be detected in body fluids such as blood plasma and urine.

It is known that endotoxin challenge induces the release of cellular iron from tissues (see, for example, Kim et al., in J. Biol. Chem. 270:5710–5713 (1995)). Thus, dithiocarbamates such as MGD are capable of removing free iron in vivo, particularly during the infectious and inflammatory conditions where intracellular iron loss is common, therefore preventing iron-induced oxidative damage to the tissues. Additionally, MGD is safe inasmuch as injections of up to 1% of the body weight in rats did not produce any ill-effects (see, for example, Komarov and Lai, in Biochim. Biophys. Acta 1272:29–36 (1995)).

Another major complication in the therapeutic use of chelators is the propensity of chelators to affect not only the desired metal but also many other essential metals, their associated metabolic pathways and other processes. Thus, for example, the treatment with DF and LI requires zinc supplementation to prevent the occurrence of zinc deficiency diseases (see, for example, De Virgilis et al., Arch. Dis. Chil. 63:250–255 (1988); and Al-Refai et al., in Blood 80:593–599 (1992)).

The low-molecular-weight iron pool in serum is thought to be the most labile iron source during chelation therapy. Chelators that remove this low-molecular-weight iron with only a minimal effect on other essential metal contents in the body are highly desirable, particularly for the treatment of transfusion-induced iron overload, as well as iron overload induced by anthracycline anti-cancer agents, inflammatory diseases such as rheumatoid arthritis and multiple sclerosis, and the like.

BRIEF DESCRIPTION OF THE FIGURES

FIG. 1 provides UV-visible spectra of N-methyl-D-glucamine dithiocarbamate (MGD) and [MGD-Fe] complexes in aqueous solution.

FIG. 1A provides a spectrum of MGD alone. An aliquot (10 μl) of MGD (100 mM) in water was added to 2 ml of water. Water was used as the control The spectrum was recorded from 800 nm to 200 nm. Note that MGD showed an intensive absorption in the 200–300 nm range.

FIG. 1B provides a spectrum of the [MGD-Fe] complex. An aliquot (40 μl) of ferrous sulfate (10 mM) was added to 2 ml of a 0.5 mM MGD solution in water. An MGD solution (0.5 mM) without ferrous sulfate was used as the control. Note the appearance of a prominent charge transfer band at 508 nm, indicative of the formation of an iron-chelator complex.

FIG. 2 illustrates the time dependent changes of visible spectra of [MGD-Fe] complex. Thus, an MGD solution (25 mM) in water was purged with a stream of nitrogen gas for 15 min prior to addition of an aliquot of nitrogen-saturated ferrous sulfate solution in water to a final concentration of 5 mM. The superimposed spectra were obtained by repetitive scanning using a three-min scan time. Other spectrometer settings included scan speed 100 nm/min and chart speed 25 nm/cm. Note that the charge transfer peak at 508 nm increased with time, indicating the autoxidation of ferrous iron to ferric iron in the [MGD-Fe] complex.

FIG. 3 presents the results of titration experiments on the complexation between MGD and $Fe^{3+}$. Serial titration experiments were performed to determine the binding stoichiometry between MGD and $Fe^{3+}$. The MGD solution in aerated water was kept at a constant concentration of 0.5 mM to which was added various amounts of ferrous sulfate ($Fe^{2+}$) from 0.05 mM to 0.5 mM with a tenth increment The mixtures of MGD and $Fe^{2+}$ were incubated at 22° C. for 10 min to allow the time required for reaching an equilibrium between the [MGD-$Fe^{2+}$] and [MGD-$Fe^{3+}$] complexes. The O.D. at 508 nm was plotted against the Fe/MGD ratios.

DETAILED DESCRIPTION OF THE INVENTION

In accordance with the present invention, there are provided methods for the in vivo reduction of free iron ion levels in a subject. Invention methods comprise:

administering to a subject an effective amount of at least one physiologically compatible compound capable of binding free iron ions.

Exemplary physiologically compatible compounds contemplated for use in the practice of the present invention are dithiocarbamates. These materials are said to be "physiologically compatible" because they do not induce any significant side effects. In other words, the main effect exerted by these compounds is to bind free iron ions.

As used herein, the phrase "free iron ions" refers to transient iron species which are not stably incorporated into a biological complex (e.g., hemoglobin, ferritin, and the like). Scavengers contemplated for use herein are highly selective for "free iron ions", relative to other forms of iron present in a physiological system.

Dithiocarbamate compounds contemplated for use in the practice of the present invention include any physiologically compatible derivative of the dithiocarbamate moiety (i.e., $(R)_2N-C(S)-SH$). Such compounds can be described with reference to the following generic structure:

$$[R_1R_2N-C(S)-S^-]M^{+1} \quad (I)$$

wherein:

each of $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl or $R_1$ and $R_2$ can cooperate to form a 5-, 6- or 7-membered ring including N, $R_1$ and $R_2$, and M is a monovalent cation.

Presently preferred compounds having the above-described generic structure are those wherein:

each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, and $M=H^+$ or $Na^+$.

Especially preferred compounds having the above-described generic structure are those wherein:

$R_1$=a $C_2$ up to $C_8$ alkyl or substituted alkyl, wherein the substituents are selected from carboxyl, acetyl, pyridinyl, pyrrolidinyl, amino, amido, hydroxy or nitro, $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$, and $M=H^+$ or $Na^+$.

The presently most preferred compounds having the above-described generic structure are those wherein:

$R_1$ =a $C_2$ up to $C_8$ alkyl or substituted alkyl, wherein the substituents are selected from carboxyl, acetyl, amido or hydroxy, $R_2$=a $C_1$ up to $C_4$ alkyl or substituted alkyl, and $M=H^+$ or $Na^+$.

When $R_1$ and $R_2$ cooperate to form a 5-, 6- or 7-membered ring, the combination of $R_1$ and $R_2$ can be a variety of saturated or unsaturated 4, 5 or 6 atom bridging species selected from alkenylene or —O—, —S—, —C(O)— and/or —N(R)-containing alkylene moieties, wherein R is hydrogen or a lower alkyl moiety.

Monovalent cations contemplated for incorporation into the above compounds include $H^+$, $Na^+$, $NH_4^+$, tetraalkyl ammonium, and the like.

As employed herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above As employed herein, "alkenyl" refers to straight or branched chain hydrocarbyl groups having at least one carbon—carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "acyl" refers to alkyl-carbonyl species.

As employed herein, "halogen" refers to fluoride, chloride, bromide or iodide atoms.

In accordance with another embodiment of the present invention, there are provided methods for treating subjects having elevated circulating levels of free iron ions. Invention methods comprise:

administering to a subject an effective amount of at least one physiologically compatible compound capable of binding free iron ions.

In accordance with yet another embodiment of the present invention, there are provided methods for treating overproduction of free iron ions in a subject. Invention methods comprise:

administering to a subject an effective amount of at least one physiologically compatible compound capable of binding free iron ions.

The presence of elevated iron levels in a subject is associated with a wide range of disease states and/or indications, such as, for example, thalassemia, sickle cell anemia, repeated blood transfusions, hereditary hemochromatosise hereditary spherocytosise hemodialysis, dietary iron uptake, Iatrogenic iron uptake, intramuscular iron dextran, hemolytic disease of the newborn, and the like.

Additional indications associated with elevated levels of free iron ions include anthracycline anti-cancer therapy, inflammation, septic shock, toxic shock syndrome, rheumatoid arthritis, ulcerative colitis, inflammatory bowel disease, gastritis, adult respiratory distress syndrome, asthma, cachexia, transplant rejection, myocarditis, multiple sclerosis, diabetes mellitus, autoimmune disorders, eczema, psoriasis, glomerulonephritis, heart failure, heart disease, atherosclerosis, Crohn's disease, dermatitis, urticaria, cerebral ischemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Parkinson's disease, Huntington's disease, epilepsy, neurodegenerative disorders, gastrointestinal motility disorders, obesity, hyperphagia, ischemia/reperfusion injury, solid tumors (e.g., neuroblastoma), malaria, hematologic cancers, Alzheimer's disease, infection (including bacterial, viral, fungal and parasitic infections), myelofibrosis, lung injury, graft-versus-host disease, head injury, CNS trauma, cirrhosis, hepatitis, renal failure, liver disease (e.g., chronic hepatitis C), drug-induced lung injury (e.g., paraquat), transplant rejection and preservation, and the like.

With particular reference to cytokine therapy, the invention method will find widespread use because cytokine therapy (with consequent induction of release of free iron ions) is commonly used in the treatment of cancer and AIDS patients. Side effects due to the induction of free iron ion release are problems commonly associated with cytokine therapy (see, for example, Lissoni et al in J.

Biol. Regulators Hemeostatic Agents 7:31–33 (1993)). Thus, a large patient population exists which will benefit from invention methods.

Presently preferred indications for treatment in accordance with the present invention include administration of IL-1, administration of IL-2, administration of IL-6, administration of IL-11, administration of IL-12, administration of tumor necrosis factor, administration of interferon-alpha or interferon-gamma, arthritis, asthma, Alzheimer's disease, Parkinson's disease, multiple sclerosis, cirrhosis or allograft rejection. Especially preferred indications for treatment in accordance with the present invention include release of free iron ions associated with cytokine therapy.

In accordance with a particular aspect of the present invention, the dithiocarbamate-containing iron scavenger is administered in combination with a cytokine (e.g., IL-1, IL-2, IL-6, IL-11, IL-12, TNF or interferon-$\gamma$), an antibiotic (e.g., gentamicin, tobramycin, amikacin, piperacillin, clindamycin, cefoxitin or vancomycin, or mixtures thereof), a vasoactive agent (e.g., a catecholamine, noradrenaline, dopamine or dobutamine), or mixtures thereof. In this way, the detrimental side effects of many of the above-noted pharmaceutical agents (e.g., induction of release of free iron ions) can be prevented or reduced by the dithiocarbamate-containing scavenger. Thus, a patient being treated with any of the above-described agents could be monitored for evidence of elevated free iron ion levels. At the first evidence of such elevated levels of free iron ions, co-administration of a suitable dose of the above-described dithiocarbamate-containing scavenger could be initiated, thereby alleviating (or dramatically reducing) the side-effects of the primary therapy.

Those of skill in the art recognize that the dithiocarbamate-containing scavengers described herein can be delivered in a variety of ways, such as, for example, orally, intravenously, subcutaneously, parenterally, rectally, by inhalation, and the like.

Since individual subjects may present a wide variation in severity of symptoms and each drug has its unique therapeutic characteristics, the precise mode of administration and dosage employed for each subject is left to the discretion of the practitioner. In general, the dosage of dithiocarbamate-containing scavengers employed in the practice of the present invention falls in the range of about 5 mg–18.5 g/day. Presently preferred modes of administration are oral or injection.

In accordance with still another embodiment of the present invention, there are provided physiologically active composition(s) comprising a compound having the structure I, as described above, in a suitable vehicle rendering said compound amenable to oral delivery, transdermal delivery, intravenous delivery, intramuscular delivery, topical delivery, nasal delivery, and the like. Depending on the mode of delivery employed, the dithiocarbamate-containing scavenger can be delivered in a variety of pharmaceutically acceptable forms. For example, the scavenger can be delivered in the form of a solid, solution, emulsion, dispersion, micelle, liposome, and the like.

Pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form In addition auxiliary, stabilizing, thickening and coloring agents and perfumes may be used. The active compound (i.e., compounds of structure x as described herein) is included in the pharmaceutical composition in an amount sufficient to produce the desired effect upon the process or condition of diseases.

Pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 15 4,160,452; and 4,265,874, to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin.

They may also be in the form of soft gelatin capsules wherein the active ingredient is mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium For this purpose any bland fixed oil may be employed including synthetic mono- or diglycerides, fatty acids (including oleic acid), naturally occurring vegetable oils like sesame oil, coconut oil, peanut oil, cottonseed oil, etc, or synthetic fatty vehicles like ethyl oleate or the like. Buffers, preservatives, antioxidants, and the like can be incorporated as required.

Compounds contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, it is up to the practitioner to determine a subject's response to treatment and vary the dosages accordingly Typical daily doses, in general, lie within the range of from about 80 $\mu$g up to about 300 mg per kg body weight, and, preferably within the range of from 100 $\mu$g to 10 mg per kg body weight and can be administered up to four times daily. The typical daily IV dose lies within the range of from about 10 $\mu$g to about 100 mg per kg body weight, and, preferably, within the range of from 50 $\mu$g to 10 mg per kg body weight In accordance with yet another embodiment of the present invention, there are provided compositions comprising an anthracycline anti-cancer agent and a dithiocarbamate having the structure I, as described above.

The invention will now be described in greater detail by reference to the following non-limiting examples.

EXAMPLE 1

UV-visible Spectra of N-methyl-D-glucamine dithiocarbamate and MGD-Fe Complex

Figure 1A:
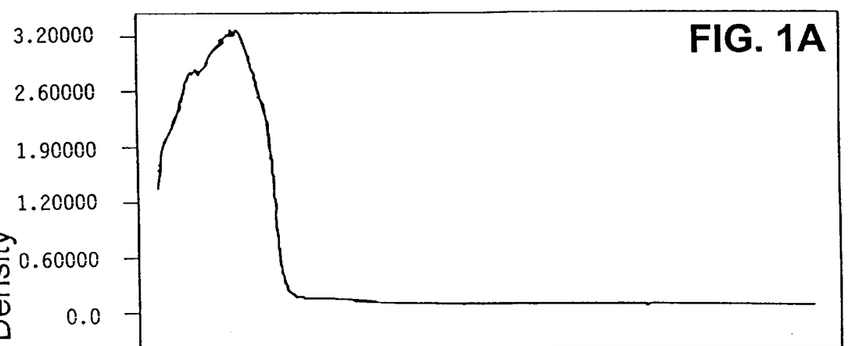

N-methyl-D-glucamine dithiocarbamate synthesized by Shinobu et al's method (Shinobu et al., supra) was highly pure as determined by element analysis and by NMR. FIG. 1A shows the UV-visible spectrum of MGD in water, which displays an intense absorption at uv regions and exhibited no absorption at the visible wavelength ranges.

Figure 1B:
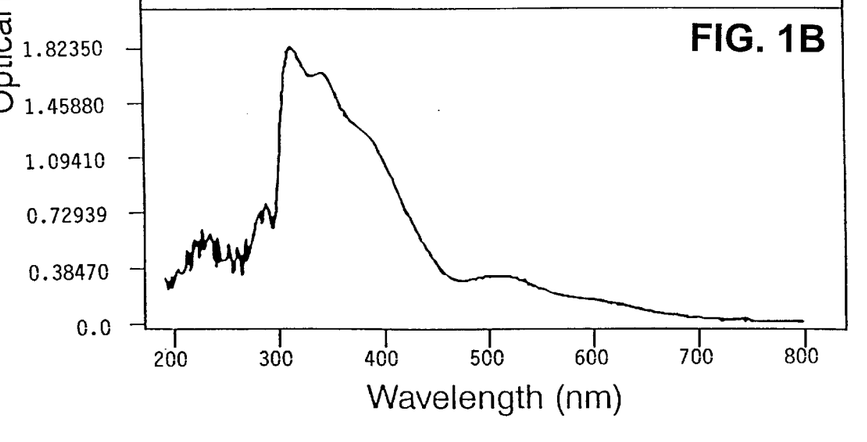

Addition of ferrous sulfate to the MGD solution under air-saturated conditions exhibits a red shift, with prominent absorption peaks appearing in the 300–400 nm range and a charge transfer band appearing at 508 nm, which is characteristic of the presence of the iron-chelator complex (FIG. 1B).

EXAMPLE 2

Figure 2:
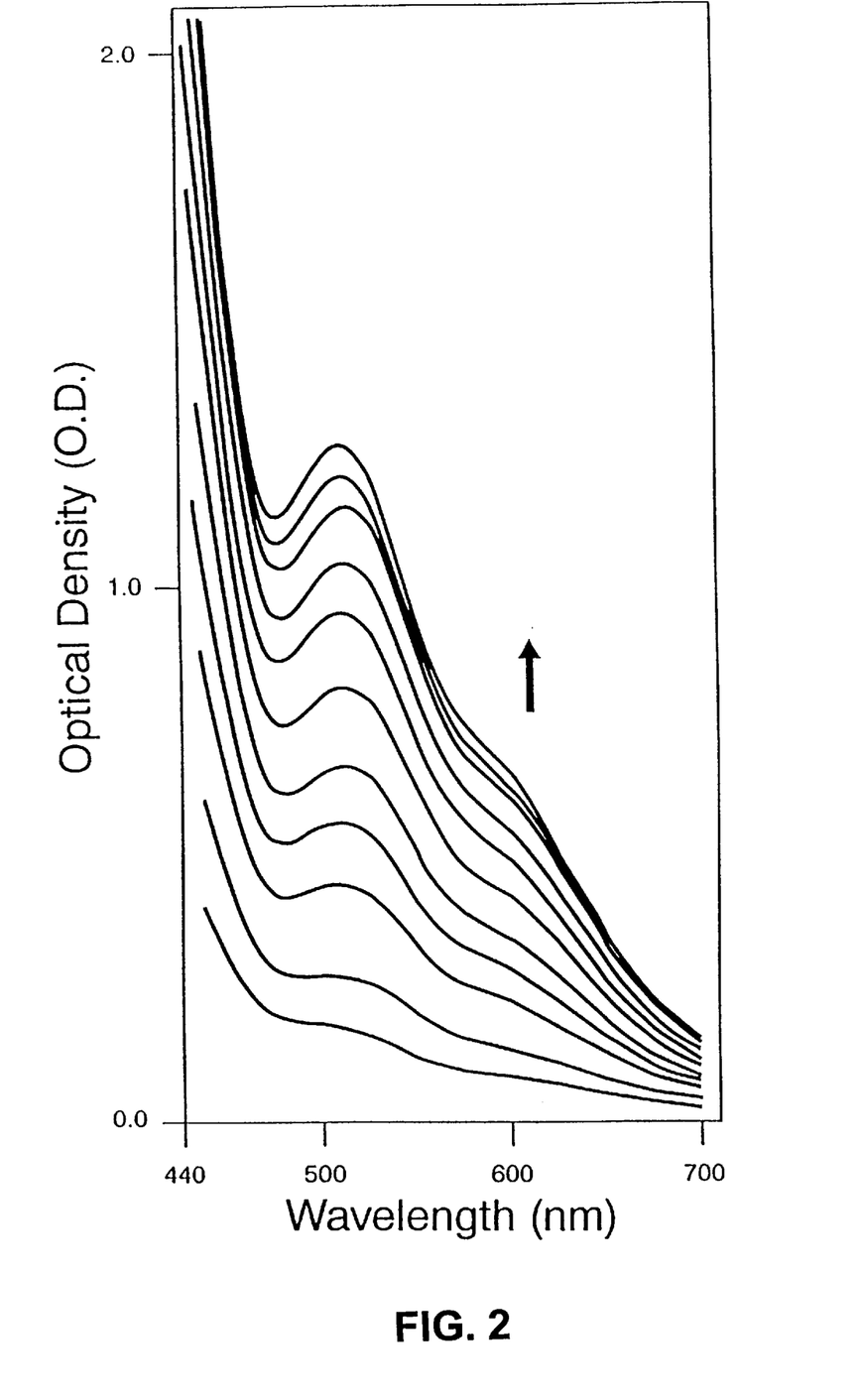

Autoxidation of the [MGD-Fe$^{2+}$] Complex to the [MGD-Fe$^{3+}$] Complex in Aqueous Solution A mixture of MGD (25 mM) and Fe (5 mM) in aerated water exhibited a prominent charge transfer band at 508 nm, indicative of the presence of the [MGD-Fe$^{3+}$] complex. The [MGD-Fe$^{2+}$] complex (25 mM/5 mM) in water prepared under anaerobic conditions exhibited no absorption peak at 508 nm. However, when the above solution was exposed to the atmospheric oxygen, the visible regions of the absorption spectra changed with time as shown in FIG. 2, in which a charge transfer peak at 508 nm increased with time. This appearance of the absorption peak at 508 nm suggests the occurrence of the autoxidation of ferrous to ferric iron in the presence of oxygen. After 30 min incubation, about 25% of the [MGD-$Fe^{2+}$] complex was converted to the [MGD-$Fe^{3+}$] complex based on the calculation of the absorption intensity at 508 nm compared to that obtained from the known concentration of the [MGD-$Fe^{3+}$] complex The results here suggest that [MGD-$Fe^{2+}$] can be autoxidated to [MGD-$Fe^{3+}$] and that MGD is capable of chelating either $Fe^{2+}$ or $Fe^{3+}$ ions forming stable complexes.

EXAMPLE 3

Binding Stoichiometry of the MGD-Fe Complex

Figure 3:
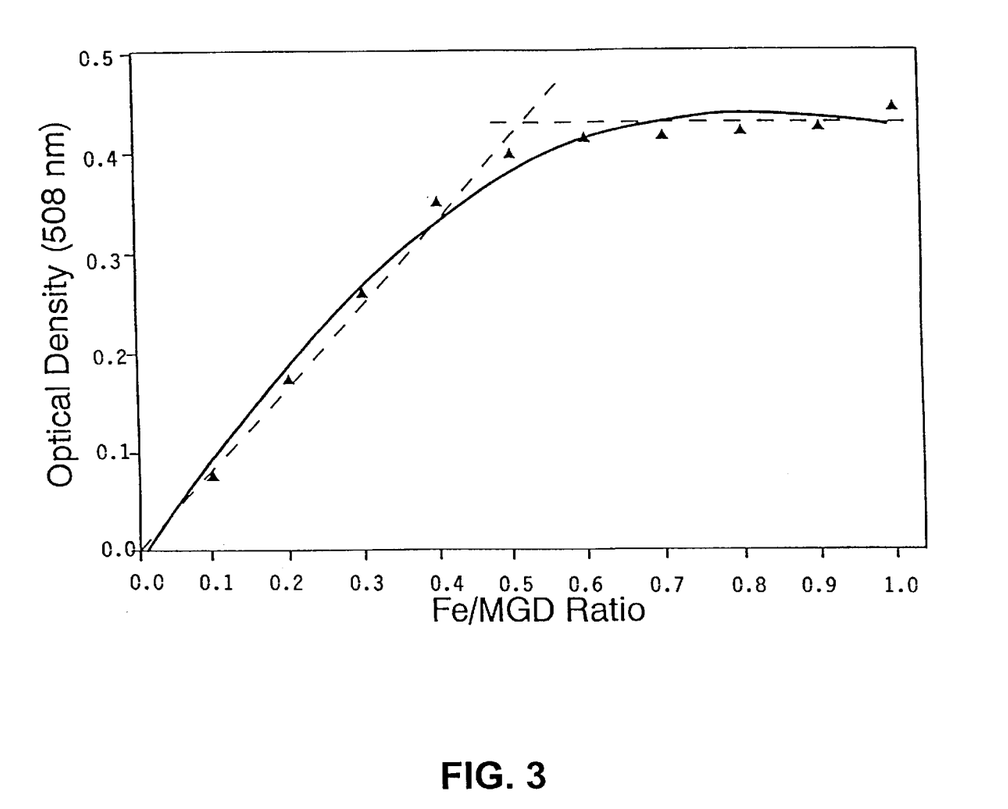

The binding stoichiometry between MGD and Fe was determined by varying concentrations of ferrous sulfate from 0.05 mM to 0.5 mM and by keeping a constant concentration of MGD (0.5 mM) in water. After 10 min incubation time, the O.D. at 508 nm of the samples were recorded and plotted as a function of the ratios of the Fe/MGD as shown in FIG. 3. The extrapolation of the initial linear region showed the stoichiometry of Fe bound to MGD was 0.5 to 1. It is concluded that two MGD molecules bind one Fe to form a two-to-one [$(MGD)_2$-Fe] complex.

EXAMPLE 4

In Vivo Chelation of Endogenous Iron by MGD in LPS-induced Shock Rats

As previously described (see Komarov and Lai in Biochim. Biophys Acta 1272:29–36 (1995), subcutaneous administration of the [$(MGD)_2$/Fe] complex reduced the in vivo .NO levels in LPS-treated mice. Since excessive .NO production is known to induce systemic hypotension, injections of the [$(MGD)_2$/Fe] complex that reduce in vivo .NO levels should also restore blood pressure in hypotensive animals induced by LPS treatment. To test this idea, experiments were carried out to determine the effects of administration of the [$(MGD)_2$/Fe] complex on the blood pressure of the hypotensive rats induced by LPS challenge.

Thus, male Wistar rats (230–300 g) fasted overnight were anesthetized with thiobutabarbital (Inactin, 100 mg/kg, i.p.). A catheter was implanted in the femoral vein for drug infusions The femoral artery was cannulated for continuous blood pressure measurement. Rats were injected with an i.v. bolus dose of LPS (S. Typhosa endotoxin, 4 mg/kg). Two hours after LPS challenge, rats were then subjected to one of the following treatments:

(a) Control, saline infusion—10 ml saline i.v. injection followed by 1.0 ml/hr of saline infusion for 1.5 hours, (b) [$(MGD)_2$/Fe] (at a ratio of 2-to-0.4)–0.1 mmole/kg i.v. bolus injection followed by 0.1 mmole/kg infusion for 1.5 hours, (c) [$(MGD)_2$/Fe] (at a ratio of 2-to-0.2)–0.1 mmole/kg i.v. bolus injection followed by 0.1 mmole/kg infusion for 1.5 hours, and (d) [$(MGD)_2$/Fe] (at a ratio of 2-to-0)–0.1 mmole/kg i.v. bolus injection followed by 0.1 mmole/kg infusion for 1.5 hours.

The mean arterial pressure (MAP) as a result of each of these treatments is summarized in Table 1.

TABLE 1

Effects of various ratios of [$(MGD)_2$/Fe] treatment on the mean arterial pressure (MAP in mmHg) in lipopolysaccharide (LPS)-induced shocked rats.

| Conditions[1] | Baseline[2] (mean ± SEM) | 2 hrs after LPS Treatment | 1.5 hrs after Treatment |
|---|---|---|---|
| a) Control saline (n = 16)[3] | 96 ± 2 | 77 ± 2 | 78 ± 4 |
| b) [$(MGD)_2$/Fe] (2/0.4)[4] (n = 16) | 95 ± 3 | 75 ± 2 | 96 ± 3 |
| c) [$(MGD)_2$/Fe] (2/0.2) (n = 6) | 98 ± 3 | 73 ± 4 | 87 ± 4 |
| d) MGD (2/0) (n = 6) | 102 ± 5 | 73 ± 2 | 94 ± 6 |

[1]Experimental conditions were as described in the text.
[2]The values of MAP prior to LPS treatment.
[3]n, the number of animals in each group.
[4][$(MGD)_2$/Fe] (2/0.4) is defined as the ratio of [$(MGD)_2$/Fe] to be 2-to-0.4.

The MAP of anesthetized rats was in the range of 96 to 102 mmHg. Two hours after LPS treatment, the MAP decreased to between 73 and 77 mmHg, which is indicative of the onset of systemic hypotension, caused by abnormally elevated levels of nitric oxide. While the 1.5 hr saline infusion did not change the MAP, infusions of [$(MGD)_2$/Fe] complex at various ratios, ranging from 2-to-0.4 (MGD to Fe) to 2-to-0 (MGD to Fe) restored the blood pressure to 87–96 mmHg (Table 1). These results suggest that the i.v. infusion of MGD either with or without added iron (Fe) can restore blood pressure in hypotensive rats induced by LPS challenge (Table 1).

Since MGD contains no reduced iron, it therefore cannot bind nitric oxide. The restoration of the MAP by the infusion of MGD can be attributed to the chelation by MGD of the cellular iron released by excessive NO production, which is known to attack cellular iron-containing proteins and result in cellular iron loss during sepsis or septic shock (see, for example, Kim et al., in *J. Biol. Chem.* 270:5710–5713 (1995)). In other words, upon intravenous infusion, the MGD molecule binds to endogenous adventitious iron released from ferritin, transferrin or other iron-containing proteins to form the [$(MDG)_2$/Fe] complex, which traps NO in vivo, forming the [$(MGD)_2$/Fe-NO] complex. The heme group of hemoglobin in the red blood cell is not accessible to MGD inasmuch as the incubation of MGD with hemoglobin solution did not produce any measurable formation of the [$(MGD)_2$/Fe] complex, presumably because of the high affinity of iron bound to the hemoglobin molecule. Thus, removal of free iron in vivo, which is known to cause oxidative damage to tissues, may be an additional advantage of the use of MGD as a therapeutic agent for the treatment of iron-overload or non iron-overload diseases and conditions, such as septic shock, hemodialysis, stroke, and thalassemia.

EXAMPLE 5

Comparison of MGD and ICRF-187 for the Promotion of Hydroxy Radical Formation via the Fention Reaction The treatment of ICRF-187 was effective in removing iron from the anthracycline-iron complex, preventing the cardiac toxicity in patients with advanced breast cancer receiving 5-fluorouracil, doxorubicin and cyclophosamide (see, for example, Kolaric et al., supra). Once it has entered the cell, ICRF-187 is converted into ICRF-198, which chelates iron intracellularly to form Fe (ICRF-198) complex. The Fe (ICRF-198) complex was 150% as effective as noncyclic iron in promoting .OH radical production in the Fenton reaction (see, for example, Thomas et al., supra). Using the same Fenton reaction as a chemical model system for hydroxyl radical production and DMPO (i.e., 5,5-dimethyl-1-pyrroline N-oxide) as a spin trap reagent, it was found that ferrous iron chelated by MGD as the [(MGD)$_2$/Fe] complex substantially reduces the reactivity of the iron species toward hydrogen peroxide to generate .OH radical, compared to free ferrous iron. These results suggest that the [(MGD)$_2$/Fe] complex is less likely to cause oxidative damage in tissues compared to the Fe (ICRF-198) complex.

While the invention has been described in detail with reference to certain preferred embodiments thereof, it will be understood that modifications and variations are within the spirit and scope of that which is described and claimed.

That which is claimed is:

1. A method for the in vivo reduction of free iron ion levels in a subject, wherein said free iron ion levels are elevated above normal, said method comprising:

administering to said subject an effective amount of at least one physiologically compatible dithiocarbamate capable of binding free iron ions, wherein said dithiocarbamate has the formula:

$$[R_1R_2N-C(S)-S^-]M^{+1} \qquad (I)$$

wherein:

each of $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkyaryl, substituted alkyaryl, arylalkyl, substituted arylalkyl, arylalkenyl, substituted arylalkenyl, arylalkynyl, substituted arylalkynyl, aroyl, substituted aroyl, acyl, substituted acyl or $R_1$ and $R_2$ can cooperate to form a 5-, 6- or 7-membered ring including N, $R_1$ and $R_2$, and M is a monovalent cation.

2. A method according to claim 1 wherein:

each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, and M=H$^+$ or Na$^+$.

3. A method according to claim 1 wherein:

$R_1$=a $C_2$ up to $C_8$ alkyl or substituted alkyl, wherein the substituents are selected from carboxyl, acetyl, pyridinyl, pyrrolidinyl, amino, amido, hydroxy or nitro, $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$, and M=H$^+$ or Na$^+$.

4. A method according to claim 1 wherein:

$R_1$=a $C_2$ up to $C_8$ alkyl or substituted alkyl, wherein the substituents are selected from carboxyl, acetyl, amido or hydroxy, $R_2$=a $C_1$ up to $C_4$ alkyl or substituted alkyl, and M=H$^+$ or Na$^+$.

5. A method according to claim 1 wherein said elevated level of free iron ions is associated with thalassemia, sickle cell anemia, repeated blood transfusions, hereditary hemochromatosis, hereditary spherocytosis, hemodialysis, dietary iron uptake, latrogenic iron uptake, intramuscular iron dextran, or hemolytic disease of the newborns.

6. A method according to claim 1 wherein said elevated level of free iron ions is associated with inflammation, septic shock, toxic shock syndrome, rheumatoid arthritis, ulcerative colitis, inflammatory bowel disease, gastritis, adult respiratory distress syndrome, asthma, cachexia, transplant rejection, myocarditis, multiple sclerosis, diabetes mellitus, autoimmune disorders, eczema, psoriasis, glomerulonephritis, heart failure, heart disease, atherosclerosis, Crohn's disease, dermatitis, urticaria, cerebral ischemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Parkinson's disease, Huntington's disease, epilepsy, neurodegenerative disorders, gastrointestinal motility disorders, obesity, hyperphagia, ischemia/reperfusion injury, solid tumors, malaria, hematologic cancers, Alzheimer's disease, infection, myelofibrosis, lung injury, graft-versus-host disease, head injury, CNS trauma, cirrhosis, hepatitis, renal failure, liver disease, drug-induced lung injury, or transplant rejection and/or preservation.

7. A method according to claim 1 wherein said elevated level of free iron ions is associated with anthracyline anti-cancer therapy.

8. A method according to claim 1 wherein said elevated level of free iron ions is associated with cytokine therapy.

9. A method according to claim 1 wherein said iron ion scavenger is administered in combination with a cytokine, an antibiotic, a vasoactive agent, or mixtures thereof.

10. A method according to claim 9 wherein said cytokine is selected from IL-1, IL-2, IL-6, IL-12, TNF or interferon-γ.

11. A method according to claim 9 wherein said vasoactive agent is selected from a catecholamine noradrenaline, dopamine or dobutamine.

12. A method according to claim 1 wherein said iron ion scavenger is delivered orally, intravenously, subcutaneously, parenterally, rectally or by inhalation.

13. A method according to claim 1 wherein said iron ion scavenger is delivered in the form of a solid, solution, emulsion, dispersion, micelle or liposome.

14. A method for treating a subject having elevated circulating levels of free iron ions, said method comprising:

administering to said subject an effective amount of at least one physiologically compatible dithiocarbamate capable of binding free iron ions, wherein said dithiocarbamate has the formula:

$$[R_1R_2N-C(S)-S^-]M^{+1} \qquad (I)$$

wherein:

each of $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkyaryl, substituted alkyaryl, arylalkyl, substituted arylalkyl, arylalkenyl, substituted arylalkenyl, arylalkynyl, substituted arylalkynyl, aroyl, substituted aroyl, acyl, substituted acyl or $R_1$ and $R_2$ can cooperate to form a 5-, 6- or 7-membered ring including N, $R_1$ and $R_2$, and M is a monovalent cation.

15. A method for treating overproduction of free iron ions in a subject, said method comprising:

administering to said subject an effective amount of at least one physiologically compatible dithiocarbamate capable of binding free iron ions, wherein said dithiocarbamate has the formula:

(I)

wherein:
each of $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkyaryl, substituted alkyaryl, arylalkyl, substituted arylalkyl, arylalkenyl, substituted arylalkenyl, arylalkynyl, substituted arylalkynyl, aroyl, substituted aroyl, acyl, substituted acyl or $R_1$ and $R_2$ can cooperate to form a 5-, 6- or 7-membered ring including N, $R_1$ and $R_2$, and
M is a monovalent cation.

16. A method according to claim 14 wherein:
each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, and
M=$H^+$ or $Na^+$.

17. A method according to claim 14 wherein:
$R_1$=a $C_2$ up to $C_8$ alkyl or substituted alkyl, wherein the substituents are selected from carboxyl, acetyl, pyridinyl, pyrrolidinyl, amino, amido, hydroxy or nitro,
$R_2$ is selected from a $C_1$ up to $C_6$ alkyl or substituted alkyl, or $R_2$ can cooperate with $R_1$ to form a 5-, 6- or 7-membered ring including N, $R_2$ and $R_1$, and
M=$H^+$ or $Na^+$.

18. A method according to claim 14 wherein:
$R_1$=a $C_2$ up to $C_8$ alkyl or substituted alkyl, wherein the substituents are selected from carboxyl, acetyl, amido or hydroxy,
$R_2$=a $C_1$ up to $C_4$ alkyl or substituted alkyl, and
M=$H^+$ or $Na^+$.

19. A method according to claim 14 wherein said elevated level of free iron ions is associated with thalassemia, sickle cell anemia, repeated blood transfusions, hereditary hemochromatosis, hereditary spherocytosis, hemodialysis, dietary iron uptake, latrogenic iron uptake, intramuscular iron dextran, or hemolytic disease of the newborn.

20. A method according to claim 14 wherein said elevated level of free iron ions is associated with inflammation, septic shock, toxic shock syndrome, rheumatoid arthritis, ulcerative colitis, inflammatory bowel disease, gastritis, adult respiratory distress syndrome, asthma, cachexia, transplant rejection, myocarditis, multiple sclerosis, diabetes mellitus, autoimmune disorders, eczema, psoriasis, glomerulonephritis, heart failure, heart disease, atherosclerosis, Crohn's disease, dermatitis, urticaria, cerebral ischemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Parkinson's disease, Huntington's disease, epilepsy, neurodegenerative disorders, gastrointestinal motility disorders, obesity, hyperphagia, ischemia/reperfusion injury, solid tumors, malaria, hematologic cancers, Alzheimer's disease, infection, myelofibrosis, lung injury, graft-versus-host disease, head injury, CNS trauma, cirrhosis, hepatitis, renal failure, liver disease, drug-induced lung injury, or transplant rejection and/or preservation.

21. A method according to claim 14 wherein said elevated level of free iron ions is associated with anthracyline anti-cancer therapy.

22. A method according to claim 14 wherein said elevated level of free iron ions is associated with cytokine therapy.

23. A method according to claim 14 wherein said dithiocarbamate is administered in combination with a cytokine, an antibiotic, a vasoactive agent, or mixtures thereof.

24. A method according to claim 23 wherein said cytokine is selected from IL-1, IL-2, IL-6, IL-12, TNF or interferon-γ.

25. A method according to claim 23 wherein said vasoactive agent is selected from a catecholamine, noradrenaline, dopaamine or dobutamine.

26. A method according to claim 14 wherein said dithiocarbamate is delivered orally, intravenously, subcutaneously, parenterally, rectally or by inhalation.

27. A method according to claim 14 wherein said dithiocarbamate is delivered in the form of a solid, solution, emulsion, dispersion, micelle or liposome.

28. A method according to claim 15 wherein:
each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, and
M=$H^+$ or $Na^+$.

29. A method according to claim 15 wherein:
$R_1$=a $C_2$ up to $C_8$ alkyl or substituted alkyl, wherein the substituents are selected from carboxyl, acetyl, pyridinyl, pyrrolidinyl, amino, amido, hydroxy or nitro,
$R_2$ is selected from a $C_1$ up to $C_6$ alkyl or substituted alkyl, or $R_2$ can cooperate with $R_1$ to form a 5-, 6- or 7-membered ring including N, $R_2$ and $R_1$, and
M=$H^+$ or $Na^+$.

30. A method according to claim 15 wherein:
$R_1$=a $C_2$ up to $C_8$ alkyl or substituted alkyl, wherein the substituents are selected from carboxyl, acetyl, amido or hydroxy,
$R_2$=a $C_1$ up to $C_4$ alkyl or substituted alkyl, and
M=$H^+$ or $Na^+$.

31. A method according to claim 15 wherein said overproduction of free iron ions is associated with thalassemia, sickle cell anemia, repeated blood transfusions, hereditary hemochromatosis, hereditary spherocytosis, hemodialysis, dietary iron uptake, latrogenic iron uptake, intramuscular iron dextran, and hemolytic disease of the newborn.

32. A method according to claim 15 wherein said overproduction of free iron ions is associated with inflammation, septic shock, toxic shock syndrome, rheumatoid arthritis, ulcerative colitis, inflammatory bowel disease, gastritis, adult respiratory distress syndrome, asthma, cachexia, transplant rejection, myocarditis, multiple sclerosis, diabetes mellitus, autoimmune disorders, eczema, psoriasis, glomerulonephritis, heart failure, heart disease, atherosclerosis, Crohn's disease, dermatitis, urticaria, cerebral ischemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Parkinson's disease, Huntington's disease, epilepsy, neurodegenerative disorders, gastrointestinal motility disorders, obesity, hyperphagia, ischemia/reperfusion injury, solid tumors, malaria, hematologic cancers, Alzheimer's disease, infection, myelofibrosis, lung injury, graft-versus-host disease, head injury, CNS trauma, cirrhosis, hepatitis, renal failure, liver disease, drug-induced lung injury, or transplant rejection and preservation.

33. A method according to claim 15 wherein said overproduction of free iron ions is associated with anthracyline anti-cancer therapy.

34. A method according to claim 15 wherein said overproduction of free iron ions is associated with cytokine therapy.

35. A method according to claim 15 wherein said dithiocarbamate is administered in combination with a cytokine, an antibiotic, a vasoactive agent, or mixtures thereof.

36. A method according to claim 35 wherein said cytokine is selected from IL-1, IL-2, IL-6, IL-12, TNF or interferon-γ.

37. A method according to claim 35 wherein said vasoactive agent is selected from a catecholamine, noradrenaline, dopamine or dobutamine.

38. A method according to claim 15 wherein said dithiocarbarnate is delivered orally, intravenously, subcutaneously, parenterally, rectally or by inhalation.

39. A method according to claim 15 wherein said dithiocarbamate is delivered in the form of a solid, solution, emulsion, dispersion, micelle or liposome.

40. A composition comprising adriamycin or liposomal adriamycin, plus dithiocarbamate.

* * * * *